United States Patent [19]
Gupta

[11] Patent Number: 5,468,887
[45] Date of Patent: Nov. 21, 1995

[54] PRODUCTION OF FATTY ACID METHYL ESTERS AND SOAPS THEREFROM

[75] Inventor: Shyam K. Gupta, Scottsdale, Ariz.

[73] Assignee: The Dial Corp., Phoenix, Ariz.

[21] Appl. No.: 851,463

[22] Filed: Mar. 13, 1992

[51] Int. Cl.$^6$ ..................................................... C07C 51/00
[52] U.S. Cl. .......................... 554/169; 554/156; 554/167; 554/170
[58] Field of Search .................................... 554/156, 167, 554/169, 174, 170

[56] References Cited

U.S. PATENT DOCUMENTS

| | | | |
|---|---|---|---|
| 2,360,844 | 10/1944 | Bradshaw et al. | 554/156 |
| 4,397,760 | 8/1983 | Story et al. | 252/370 |
| 4,474,683 | 10/1984 | Story et al. | 252/369 |
| 4,772,434 | 9/1988 | Myers | 264/8 |

FOREIGN PATENT DOCUMENTS

| 3707563 | 9/1988 | Germany | 554/169 |
|---|---|---|---|

OTHER PUBLICATIONS

"Ester Reactions of Fatty Materials", Marvin W. Formo, The Journal of the American Oil Chemists Society, vol. 31, Jan. 1954, pp. 548–559.
"New Soap Process", George B. Bradshaw, SOAP, May 1942, pp. 23, 24, 69 and 70.
Bailey's Industrial Oil and Fat Products, vol. 2 4th Edition, pp. 122–127, 130–133.
Fatty Acid Methylesters A Universal Raw Material for Soaps and Detergents, Davidsohn et al, Apr. 1985.
The Saponiflex Process; Soap/Cosmetics/Chemical Specialties, Apr. 1991, pp. 34–36.

Primary Examiner—José G. Dees
Assistant Examiner—D. Carr
Attorney, Agent, or Firm—Richard G. Harrer; Bernard L. Howard

[57] ABSTRACT

A method of preparing esters and water soluble soaps using intensive mixing. The esters are prepared by reacting fats & oils with methanol containing caustic as a catalyst wherein the glycerin formed is removed. The resulting esters are saponified with caustic along with an additional amount of methanol to form the soap.

11 Claims, 1 Drawing Sheet

U.S. Patent
Nov. 21, 1995
5,468,887
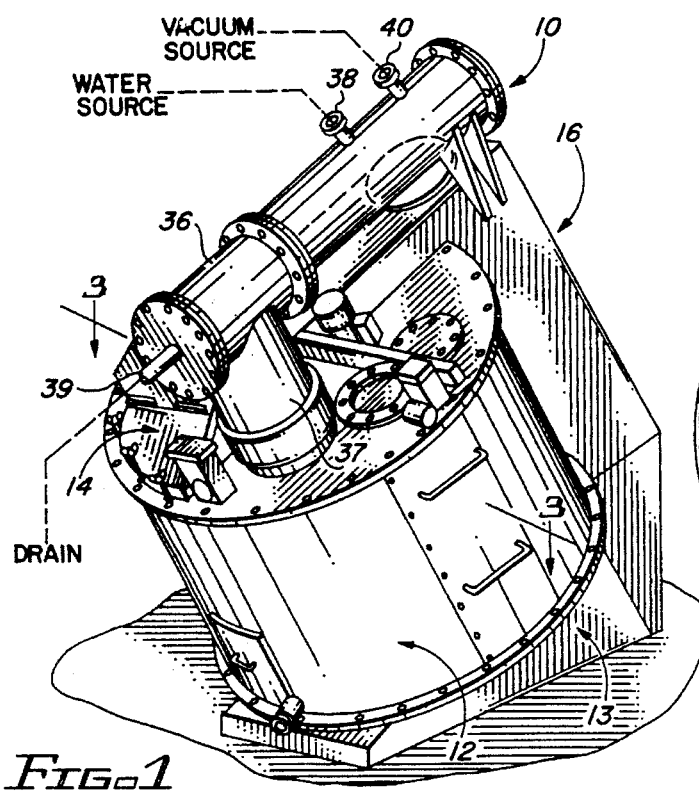
FIG. 1
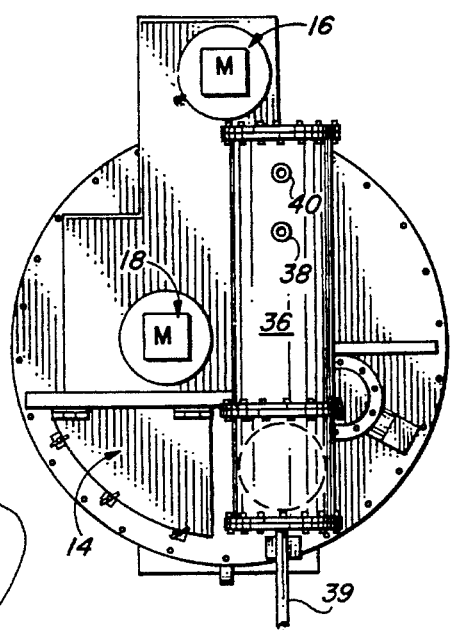
FIG. 2
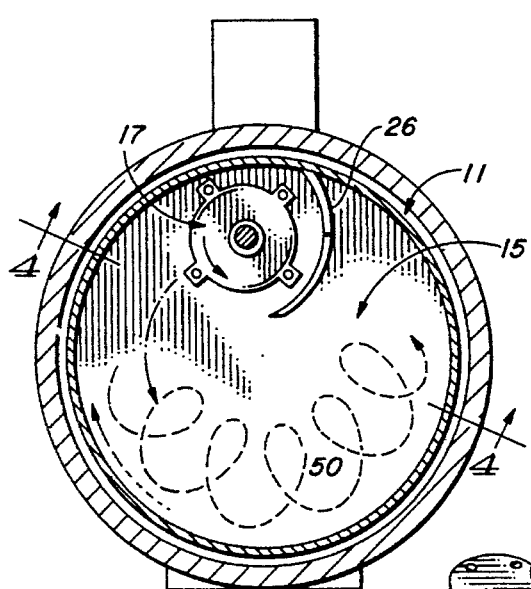
FIG. 3
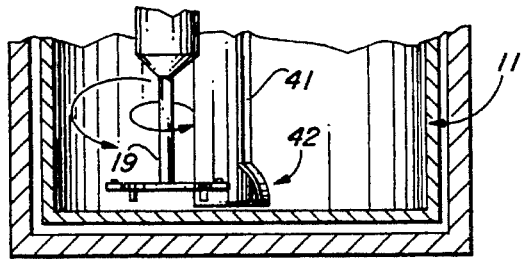
FIG. 4
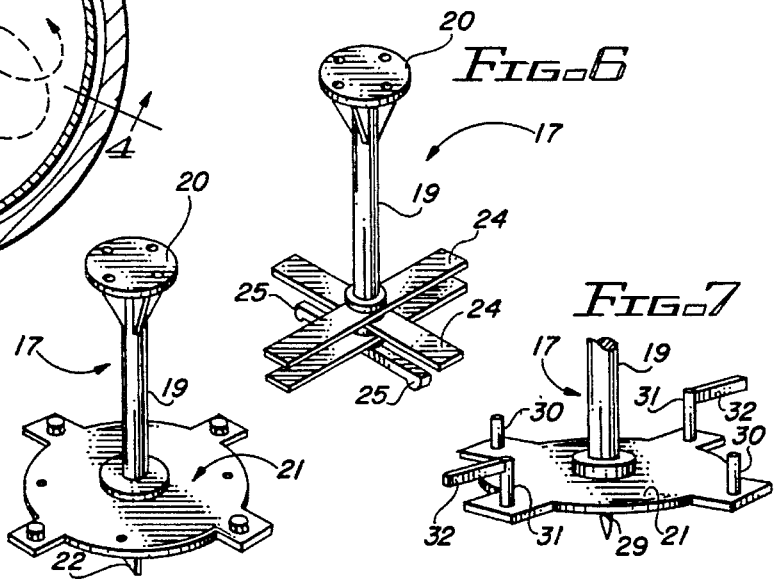
FIG. 5
FIG. 6
FIG. 7

PRODUCTION OF FATTY ACID METHYL ESTERS AND SOAPS THEREFROM

FIELD OF THE INVENTION

This invention relates to energy efficient, rapid processes for the preparation of soaps from natural fats and oils via fatty acid methyl esters. More particularly, this invention relates to such processes utilizing intensive mixing and whereby such fats and oils are initially processed to form fatty acid methyl esters, and which are thereafter saponified to form fatty acid soaps.

BACKGROUND OF THE INVENTION

The methyl ester route for soap making involves first the preparation of fatty acid methyl esters from fats and oils (ester exchange) and subsequent saponification of the methyl esters to give soap with concomitant recovery of ensuing methanol, all according to the following.

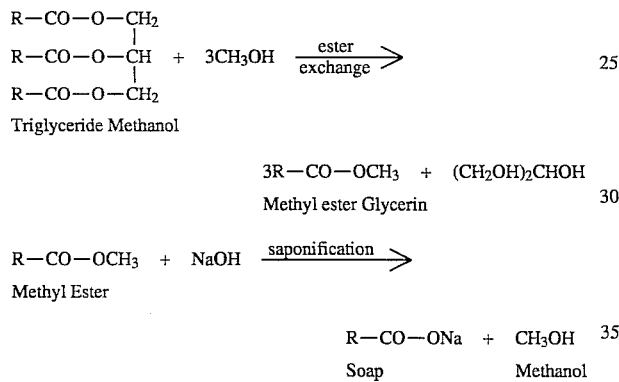

Displacement of the glycerol in a fat by a low-molecular-weight alcohol, such as methyl or ethyl alcohol, is described in Bradshaw and Meuly U.S. Pat. No. 2,271,619. The process is said to produce methyl or ethyl esters directly from the fat, without intervening hydrolysis, and is said to take place at low temperatures. Although the reaction can be carried out in open tanks constructed of ordinary carbon steel, it is preferred to use sealed vessels. The fat must be clean, dry, and substantially neutral. It is heated to about 80° C. (176° F.), and to it is added commercial anhydrous (99.7%) methyl alcohol in which is dissolved 0.1–0.5% sodium or potassium hydroxide. The quantity of alcohol recommended is about 1.6 times that theoretically required for the reaction, although it is stated the alcohol may be reduced to as little as 1.2 times theoretical, if the operation is carried out in three steps. Alcohol amounting to more than 1.75 times the theoretical quantity does not materially accelerate the reaction and is said to interfere with subsequent gravity separation of the glycerol.

The Bradshaw patent contemplates use of the methyl esters to make anhydrous soap by a continuous process. It is stated the esters are saponified by caustic soda or caustic potash at a low temperature, and the methyl alcohol can be recovered for reuse. The methyl and ethyl esters of fatty acids are fluid, relatively stable, noncorrosive, and low-boiling derivatives, and in certain operations are preferred to free fatty acids. Methyl esters are preferred over the ethyl esters for reasons of lower cost of manufacture and better pyrolytic stability during processes such as fractional distillation.

It has also been reported that the alkali-catalyzed alcoholysis method is completely successful only if the fat is almost neutral and the reaction mixture is substantially anhydrous. Failure to comply with either of these conditions causes soap formation, which leads to a loss of alkalinity and also the building up of a gel structure that prevents or retards separation and settling of the glycerol.

The saponification of fatty methyl esters with alkalis to produce soap is well-known. Equipment for this purpose is available, for example, from Lion Corporation in Japan and Ballestra in Italy. In the known processes for manufacture of soap from fatty methyl esters, the methyl esters are first reacted with an alkali which results in the production of a soap mass containing both water and methanol. In the next step, excess water and methanol are removed. Several procedures are available to accomplish this step. For example, methanol can be removed by placing the soap mass as a thin film on a rotary drum. The soap mass is thus converted to soap flakes which can then be dried further by passing the flakes through an oven.

However, the following disadvantages are noted for the saponification of methyl esters to produce soap by such prior art methods:

1. The reaction of methyl esters with alkalis cannot be accelerated since all reactions are done at ambient pressures.
2. The concentration of soap in the soap mass is usually limited to the 60–70% range in order to have proper fluidity of soap mass to flow.
3. The drying of soap mass to remove methanol and excess water is highly limited and often not easily controllable.
4. The recovery of methanol for recycling into the system is rather complicated involving multistep processing.

SUMMARY OF THE INVENTION

It has been discovered that intensive mixing can be employed to produce fatty acid methyl esters from fat and oil stocks and that the fatty methyl esters so produced can then be saponified to form soaps, again by employing intensive mixing. As used herein, intensive mixing means introducing the raw materials normally employed in producing fatty methyl esters, i.e., suitable triglycerides, methanol and a caustic catalyst, such as NaOH, into an enclosed mixing vessel equipped with a condenser. The materials in the vessel are caused to rotate in a generally circular path while simultaneously bringing the material in contact with a separate rotating means mounted within the vessel, with the rotating means rapidly rotating either counter to or in the same direction as the initial direction of flow of the materials. The equipment useful to conduct the process is described in Myers U.S. Pat. No. 4,772,434 which is incorporated herein by reference. In preparing methyl esters, the vessel shown in the Myers patent is preferably equipped with a heating jacket whereby the temperature of the reactants may be raised, if desired. Additionally, it is desirable to equip the vessel with a syphon device to enable convenient removal of glycerin after the formation of the methyl esters. It has been found that fatty acid methyl ester formation occurs rapidly, usually in from about 15 to 60 minutes and that it is relatively easy to recover and purify any excess methanol as well as glycerin.

Preferably, an excess of about 10% methanol is employed over the stoichiometric amount required for ester formation, the excess methanol serving as a reaction solvent resulting in better mixing of the reactants. Also, although not necessary, it is preferable to add an acid at the end of the reaction to neutralize any caustic since there may be some free fatty acid formed which might react with caustic to form a soap. The presence of any soap might interfere with the separation of esters and glycerin after the reaction is completed. Such acidification also prevents any formation of triglyceride since the basic reaction is somewhat reversible. The process can use a wide variety of triglycerides although the reaction is somewhat slower as the molecular weight of the triglyceride increases, likely because the solubility of the methanol in the triglyceride decreases with the higher molecular weight materials. This can be easily overcome in the process by increasing the reaction temperature or increasing the speed of the intensive mixing. A further advantage of the process includes the recovery of a high concentration of glycerin— up to about 70% versus from 8–10% in the prior art steam splitting process. The glycerin is easily recovered from the mixer either by syphon or through centrifugation. Further, we find that less water is produced in the process which makes it easier to separate and purify the methanol which is left over after completion of the reaction. Another advantage to the process involving intensive mixing is that it is possible to use a lower grade triglyceride as a starting material and end up with a higher quality ester in that any so-called "color bodies" present in the triglyceride will migrate to the glycerine and thus not be present in the ester.

Similarly the use of intensive mixing to form soap from fatty methyl esters is a very rapid reaction. Although the esters and caustic (i.e. NaOH) are rather immiscible, the employment of intensive mixing results in superior contact of the reactants and thus a rapid reaction to form soap is the result. The speed of the reaction may be increased by applying pressure to the vessel as well as by increasing the speed of the intensive mixing. When the saponification is completed, vacuum can be applied to the vessel to remove the methyl alcohol. The application of vacuum may be continued to remove some of the water present in the soap, if that is desired. As earlier noted, the intensive mixing may be either counter-current or co-current. That is where the separate rotating means mounted in the vessel is rotating in a direction counter to the direction of flow of the material, counter-current mixing is taking place. Conversely, where the rotating means is rotating in the same direction as the initial direction of flow of the material, co-current mixing is taking place. Counter-current mixing is preferred.

BRIEF DESCRIPTION OF THE DRAWINGS

FIG. 1 is a perspective view of mixing equipment adapted to provide intensive mixing to produce fatty methyl esters from suitable fat and oil stocks and to saponify such esters to produce soap;

FIG. 2 is a horizontal view of the mixing equipment of FIG. 1;

FIG. 3 is a horizontal sectional view of the mixing equipment of FIG. 1 taken substantially on the line 3—3 of FIG. 1;

FIG. 4 is a fragmentary sectional view of the mixing equipment of FIGS. 1–3 taken substantially on the line 4—4 of FIG. 3;

FIGS. 5–7 are perspective views of rotors which can be employed in the mixing equipment shown in FIGS. 1–4.

DESCRIPTION OF THE PREFERRED EMBODIMENTS

As used herein the expression "fat and oil stocks" means the raw materials which are customarily employed in soap manufacture such as the naturally occurring fats and oils which are triglycerides with three fatty groups randomly esterified with glycerol (tallow, lard, coconut oil, palm kernel oils and the like). The expression "saponify" or "saponification" means the neutralization with typical alkaline materials such as NaOH, KOH, soda ash and the like of fatty methyl esters to produce soap. By intensive mixing is meant causing a liquid stream of the reactants to rapidly move in a circular direction (e.g., counterclockwise) within a mixing vessel and at the same time bringing this rapidly moving stream into contact with mixing means rotating either in a direction counter to or in the same direction as the rapidly moving stream of reactants.

Referring to the drawings, FIG. 1 shows an embodiment of the mixing equipment useful in this invention and is designated generally at 10. The mixer 10 can be described as a mixing pan 11 (see FIGS. 3–4) rotatably mounted within sealable vessel 12 which is in turn, mounted on frame 13. The frame 13 is inclined so that the mixing pan 11 is tilted from the horizontal, thereby using gravity to assist in working the reactants within the mixing pan. Access to the interior of the mixer and more specifically to the mixing pan 11 is provided by hinged loading door 14, which is designed to provide an air tight seal when closed. The equipment is further provided with a water and air tight discharge gate 15 (see FIG. 3) at the bottom of the mixing pan. The discharge gate allows for removal of the soap after saponification has been completed.

The mixing pan 11 is driven by motor 16 mounted adjacent to the vessel 12. The required horsepower of this motor is of course dependent on the size of the mixing pan employed and the characteristics of the batch of ingredients being processed. As previously mentioned, the mixing pan is rotatably mounted and in the particular embodiment illustrated in FIG. 3, rotates in a clockwise manner. Mounted to the top of mixer 10 and eccentrically within mixing pan 11 is rotor assembly 17. The rotor assembly 17 is provided with a separate variable speed motor 18 (see FIG. 2) so that the speed of the rotor assembly may be changed as desired. Referring to FIG. 5, the rotor assembly consists of shaft 19 and attachment member 20 for securing the assembly to the drive motor. Various type of mixing tools may be mounted on shaft 19, of which FIGS. 5–7 are examples.

The mixing tool of FIG. 5 consists of generally circular plate 21 beneath which are mounted pins 22. FIG. 3 and FIG. 4 show a rotor assembly as disclosed in FIG. 5 and it is noted that the assembly is eccentrically mounted within the mixing pan and rotates in a direction counter to the direction of rotation of the mixing pan.

In FIG. 6 the mixing tool consists of two pairs of arms or knives 24 which are mounted at substantially right angles to each other and can be provided with balance weights 25 to counterbalance the assembly if such is necessary.

There is no significant difference in the mixing abilities of the mixing tools of FIGS. 5 and 6 although the mixing patterns are somewhat different.

It will be appreciated that a rotor assembly performs three functions in countercurrent or co-current mixing; that is, liquid mixing, and where soap is being made, dough chopping, and granulation of a soap product. A rotor assembly which is well adapted to perform these functions is shown in FIG. 7. The mixing tool of FIG. 7 consists of circular plate 21 beneath which are mounted pins 29. Above the plate 21 are mounted pins 30 and pins 31, pins 31 having horizontal chopper blades 32 secured to the top thereof. These chopper blades are mounted at the top of the pins 31, so as not to contact the fluid mixture until it is semi-solid and non-sticky.

Referring to FIGS. 1 and 2, it is seen that above the sealable vessel 12 is mounted a condenser 36. The mixing pan 11 (see FIGS. 3–4) is open to the condenser 36 via water vapor conduit 37. Although the interior of the condensor 36 is not shown, it is constructed in the conventional manner. Within the condenser 36 are a series of cooling tubes through which cooling water flows. The cooling water is introduced at the top of the condenser through coolant opening 38 and removed from the bottom of the condenser through a coolant drain (not shown). When the relatively warmer water vapor or excess alcohol from the mixing pan comes into contact with the cooling tubes (which must be cooled to a temperature below the dew point of the warm water vapor or alcohol vapor), the warm water vapor and/or alcohol condenses into liquid form on the tubes and the liquids can then be drained out of the condenser 36 through water drain 39.

A vacuum may be applied to the mixing equipment of FIGS. 1–4 in the following described manner. A vacuum port 40 on the condenser 36 is open to the interior chamber of the condenser, which in turn, is open to the mixing pan 11 via water vapor conduit 37. Any of the number of well known devices for creating a vacuum may be connected to the vacuum port 40 to create a vacuum. The term "vacuum" as used herein, refers to a pressure within the sealable vessel 12 which is below ambient atmospheric pressure. In the embodiment shown in FIGS. 1 and 2 a vacuum pump of conventional design was used. The sizing of the vacuum pump will depend upon the size of the mixing equipment used and on the desired vacuum level.

Mounted within mixing pan 11 are means to insure that the materials within the mixing pan are subjected to the intensive mixing operation. These means are secured to the to part of the mixing equipment immediately above the mixing pan and, as shown in FIG. 3 and FIG. 4 consist of a pan wall wiper 41 and pan bottom deflector 42 which is attached to the pan.

Referring to the equipment in FIGS. 1–4, in preparing the fatty acid esters, the fat or oil stock can be introduced through loading door 14 or through appropriate valves (not shown) mounted in the vessel 12. After the fat or oil stock has been introduced, rotation of mixing pan 11 is begun and thereafter methanol and caustic is added, either through the loading door or a valve. Rotation of the rotor assembly 17 is begun and intensive mixing of the reactants takes place. If counter-current mixing is employed, the rotation of pan 11 and rotor assembly 17 will be as shown in FIG. 3. A generally rotary movement of the reactants will be created much like a whirlpool as shown by the dotted arrow 50. The fat or oil stock employed in preparing the fatty methyl esters may be any of those customarily employed in making water soluble soaps. The fat or oil stock is preferably liquid ranging from their melting point to about 170° F. The methanol and caustic are then added and the reaction is allowed to proceed. The methanol and caustic may be added in several ways. The methanol can be heated to about 140° F. and the caustic mixed in with the methanol and then added to the mixer. Alternately, the methanol and caustic can be added separately, the methanol being added initially followed by caustic. The amount of methanol employed is about 10% in excess over the stoichiometric amount required for ester formation. Additionally, some acid such as sulfuric acid may be added after the reaction is complete to neutralize any free caustic. The addition of the acid is usually not necessary where the esters will be converted to soap after the removal of glycerin.

The preparation of soap from the fatty acid methyl esters employing intensive mixing is usually a very rapid process. Methanol is important to enhance the initiation of the reaction and caustic (NaOH) of 50% or 30% concentration work well. A higher concentration of caustic reduces the drying phase of the process, but a lower concentration (30%) facilitates homogenization during saponification.

In the following examples, all processing was conducted in a Model RO2 mixer manufactured by Eirich Machines of Hardheim, Germany. The mixer was equipped with a sealable vessel surrounding the mixing pan and a vacuum apparatus and condenser similar to that shown in FIGS. 1–4. In all examples, counter-current mixing was employed.

EXAMPLE I

Fatty methyl esters were prepared according to the following materials and procedure.

| | |
|---|---|
| 60:40 palm:palm kernel oil | 2000 g |
| NaOH pellets | 10 g |
| Methanol | 800 g |
| Sulfuric acid | 20 g |

Procedure
  Oil blend charged to mixer—pre-heated to 80° C.
  Methanol heated to 60° C., caustic added to methanol.
  Methanol/caustic mixture charged to mixer with pan and rotor low speed; —that is 36 rpm and 580 rpm respectively
  Rotor to medium speed (1140 rpm) for about 3 minutes.
  Heater turned on and 50 ml of methanol added.
  Reaction completed after approximately one hour.
  Added acid solution and reaction mixture allowed to separate.
Observations
  Reaction appeared complete after 1 hour, layering noted.
  Acid addition formed a white saponified layer between the glycerin and methyl ester layer—probably not necessary.

| | | |
|---|---|---|
| Yield | 1935 g | Methyl ester |
| | 578 g | Glycerin |
| | 2513 g | Total Yield |

EXAMPLE II

Fatty methyl esters were prepared according to the following materials and procedures.

| | |
|---|---|
| 60:40 palm:palm kernel oil | 2000 g |
| NaOH pellets | 10 g |
| Methanol | 800 g |

Procedure
  Methanol and caustic pellets pre-heated to 63° C. and charged to mixer.
  Added oil blend to mixer, pan at 36 rpm, temperature 59° C.
  Rotor at 1140 rpm.
  Samples collected every 5 minutes to identify layering.
  Reaction appeared completed after 30 minutes.
  Allowed to mix an additional 30 minutes to monitor separation.
  Product collected and allowed to separate.

Observations
Reaction facilitated in the presence of excess methanol and caustic.
Acid addition apparently not necessary.

| - Yield - | Methyl ester | 1788 g |
| --- | --- | --- |
| | Glycerin | 383 g |
| | Total Yield | 2171 g |

The yield was reduced because of sampling.

EXAMPLE III

Palm and palm kernel fatty acid methyl esters were saponified using the following materials and procedures.

| 60:40 palm:palm kernel methyl ester | 1200 g |
| --- | --- |
| 30% NaOH | 580 g |
| Methanol | 220 g |
| | 2000 g |

Procedure
Methyl esters added to mixer—had been preheated to 80° C.; pan at 36 rpm
NaOH added to the pan
Methanol added slowly—at a temperature 71° C.
Rotor to high speed (1140 rpm) after reaction initiated—maximum temperature 79° C.
Excess methanol collected
Observations
Reaction went well—completed in 30 min.
Reflux condenser not 100% efficient, need chilled water rather than ambient temperature water
Vacuum applied too quickly—evacuated mixer to condenser
Moisture and volitile (M&V) (oven) 16.1% alk. 0.15% free fat as AV 214

EXAMPLE IV

Example III was repeated using 50% NaOH.

| 60:40 palm:palm kernel ME | 1200 g |
| --- | --- |
| 50% NaOH | 348 g |
| Methanol | 220 g |
| | 2000 g |

Procedure
Methyl esters and methanol added to mixer, pre-heated to 63° C.
NaOH charged, pan on slow (36 rpm) initially, ambient temperature.
Rotor to high (1140 rpm) when reaction initiated—maximum temperature 77° C.
Excess methanol and water collected.
Observations
Reaction completed in 17 min., a faster rate than 30% NaOH
Collected 150 g methanol/H$_2$O
M&V (oven) 14.7%, alk. 0.06%
Product more fibrous than Run #1

EXAMPLE V

Example IV was repeated without excess methanol.

| 60:40 palm:palm kernel ME | 1200 g |
| --- | --- |
| 50% NaOH | 348 g |
| | 1548 g |

Procedure
Methyl esters added to mixer—preheated to 72° C.
NaOH charged slowly at 81° C.
25 g methanol added to initiate reaction
Rotor to high speed (1140 rpm) after several minutes at maximum temperature of 90° C.
100 g H$_2$O added after one hour
No drying necessary
Observations
Reaction appeared to initiate with addition of methanol, however, it would not completely react.
Added 100 g water after one hour of mixing—product changed and appeared reacted—no drying necessary.
M&V (oven)—9.4%—alk. 0.28%
Extra methanol and/or water appeared to be important in completing the reaction

EXAMPLE VI

The process of Example III was repeated without excess methanol.

| 60:40 palm:palm kernel ME | 1200 g |
| --- | --- |
| NaOH (30%) | 580 g |
| | 1780 g |

Procedure
Added methyl esters to mixer, pre-heated to 80° C.
NaOH charged slowly at ambient temperature.
Rotor to high speed (1140), no reaction after about 10 minutes
Added 150 ml methanol in increments of 25 ml until reaction initiated at approximately 30 minutes
Collected excess methanol+H$_2$O
Observations
Reaction occurred rapidly when 150 ml methanol was added to mixer and appears to be necessary for reaction. Maximum reaction temperature 87° C.—M&V (oven) 23.8%, alk. 0.04%.

EXAMPLE VII

| Methyl ester | 1200 g |
| --- | --- |
| 50% NaOH | 348 g |
| Methanol | 200 g |
| | 1748 g |

Procedure
Oil blend charged to mixer—heated to 79° C.
Methanol added—ambient temperature
NaOH charged slowly—pan rotor slow initially
Reaction completed in about 30 minutes
What is claimed is:
1. A process for making fatty acid methyl esters from fats and oils comprising introducing said fats and oils and methanol into an enclosed mixing vessel along with caustic as a catalyst, causing the foregoing materials to be subjected to intensive counter-current or co-current mixing in said vessel for a period of time sufficient to convert said fats and oils to fatty acid methyl esters, and thereafter separating glycerin from said esters.

2. The process of claim 1 wherein said materials are subjected to counter-current mixing.

3. A process for making water soluble soaps from fats and oil stocks customarily employed in making such soaps, comprising the steps of initially producing fatty acid methyl esters from said fats and oils by introducing said fats and oils and methanol into an enclosed mixing vessel along with caustic as a catalyst, causing the foregoing materials to be subjected to intensive counter-current or co-current mixing in said vessel for a period of time sufficient to convert said fats and oils to fatty acid methyl esters, removing glycerin formed during said ester production, thereafter adding caustic to said methyl esters in an amount sufficient to saponify said methyl esters along with additional methanol, and causing said materials to be subjected to counter-current or co-current intensive mixing whereby saponification of said methyl esters takes place.

4. The process of claim 3 wherein said materials are subjected to counter-current mixing.

5. The process of claim 4 wherein said vessel is equipped with a condenser and means for applying a vacuum or pressure.

6. The process according to claim 5 wherein the counter rotating means employed in counter-current mixing are mounted eccentrically within said vessel and at a distance from the wall of said vessel.

7. The process of claim 6 wherein said fat and oil stocks are liquid ranging from their melting point to about 170° F.

8. The process of claim 7 wherein the methanol added to said fat and oil stocks is in excess over the stoichiometric amount required for ester formation.

9. The process of claim 8 wherein said excess is about 10%.

10. The process of claim 9 wherein the concentration of caustic employed said saponification steps is from about 30% to about 50%.

11. The process of claim 10 wherein vacuum is applied to remove methanol formed in said saponification step and said methanol is condensed by said condenser.

* * * * *